United States Patent
Shiratani et al.

(10) Patent No.: US 6,441,187 B1
(45) Date of Patent: Aug. 27, 2002

(54) METHOD FOR PRODUCING CAMPHORSULTAM

(75) Inventors: Hiroshi Shiratani, Osaka (JP); Shigeya Yamasaki, Osaka (JP)

(73) Assignees: Sumika Fine Chemicals Co., Ltd., Osaka (JP); Ono Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/901,077

(22) Filed: Jul. 9, 2001

(30) Foreign Application Priority Data

Aug. 23, 2000 (JP) ........................................ 2000-253083

(51) Int. Cl.7 ............................................ C07D 275/06
(52) U.S. Cl. ........................................ 548/208; 548/206
(58) Field of Search .......................................... 548/208

(56) References Cited

U.S. PATENT DOCUMENTS 6,333,415 B1 * 12/2001 Yamamoto

OTHER PUBLICATIONS

Towson et al., "(+)-(2R,8aS)-10-(Camphorylsulfonyl) Oxaziridine," *Organic Syntheses*, Collect. vol. VIII, 104–110 (1993).
Weismiller et al., "(-)-D-2, 10- Camphosultam," *Organic Syntheses*, Collect. vol. VIII, 110–112 (1993).
Capet et al., "A Two–Step Synthesis of Camphosultam," *Synthetic Communications*, 25 (21), 3323–3327 (1995).
Binger et al., "Asymmetrishce Nickel(0)–katalysierte [3+2] Cycloadditionen von Methylencyclopropanen mit chiralen Acrylsäure–Derivaten," *Liebigs Annalen Der Chemi*, No. 8, 739–750 (XP–002183098) (Aug. 1989).
Vandewalle et al., "Iridoids: Enantioselective Synthesis of Loganin Via An Asymmetric Diels–Alder Reaction," *Tetrahedron*, 42 (14), 4035–4043 (XP–002183097) (1986).

* cited by examiner

Primary Examiner—Sabiha Qazi
(74) Attorney, Agent, or Firm—Leydig, Voit & Mayer, Ltd.

(57) ABSTRACT

A method for producing camphorsultam, which includes the following steps 1 to 4:

Step 1: reacting camphorsulfonic acid with a halogenation agent to give camphorsulfonyl halide, Step 2: reacting the camphorsulfonyl halide with ammonia to give camphorsulfonamide, Step 3: subjecting the camphorsulfonamide to dehydration and ring closure to give camphorsulfonimine, and Step 4: reducing the camphorsulfonimine with sodium borohydride in an aqueous isopropanol solution. According to this invention, camphorsultam and intermediates thereof can be obtained by an industrial method which is comparatively safe to the environment and human body, economical, and which is simple and easy.

12 Claims, No Drawings

METHOD FOR PRODUCING CAMPHORSULTAM

This application claims priority from JP 253083/2000 which is a Japanese applicable file on Jul. 9, 2001.

TECHNICAL FIELD OF THE INVENTION

The present invention relates to a method for producing camphorsultam and its intermediate, which are useful as a reagent for asymmetric induction and as a starting material for a compound useful as a fine chemical or medicament.

BACKGROUND OF THE INVENTION

Camphorsultam is useful as a reagent for asymmetric induction and as a starting material for a compound useful as a fine chemical or medicament. It can be produced by various known methods, wherein the following scheme is generally employed for the production. Note that the following compounds 1–5 includes S pounds, R compounds and racemates.

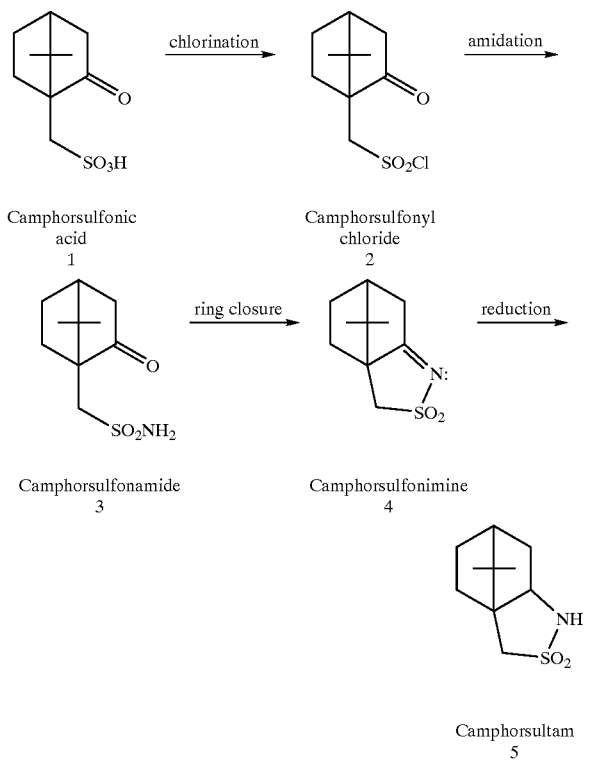

According to Towson et al., in the above-mentioned scheme,
1. 1 is reacted with 2.4 equivalents of thionyl chloride in chloroform to give 2,
2. 2 is reacted with $NH_4OH$ to give 3, and
3. 3 is reacted in the presence of AMBERLYST to give 4 (ORGANIC SYNTHESIS, COLLECT VOL. VIII, 104–105). According to Weismiller et al., in the above-mentioned scheme, 4 is reduced with $LiAlH_4$ to give 5 (ORGANIC SYNTHESIS, COLLECT VOL. VIII, 110–111).

When the above-mentioned conventional production method is practiced at an industrial level, there arise various problems that the use of chloroform is not preferable for human body and the environment, and the use of $LiAlH_4$ is dangerous.

According to Capet et al., in the above-mentioned scheme,
1. 1 is reacted with 4 equivalents of thionyl chloride without a solvent to give 2, and excess thionyl chloride is removed,
2. 2 is reacted with ammonia in a 60-fold molar amount relative to 1 in an aqueous 1,4-dioxane solution to give 3,
3. 3 is subjected to dehydration and ring closure at 90° C. to give 4, and
4. 4 is reduced with sodium borohydride in a 2-fold molar amount relative to 4 in an aqueous methanol solution to give 5 (SYNTHETIC COMMUNICATIONS, 25 (21), 3323–3327 (1995)).

When the above-mentioned production method is practiced at an industrial scale, the following problems unpreferably occur.

The chlorination in a non-solvent system is preferable, but the amount used of thionyl chloride is 2-fold molar amount relative to 1, which gives rise to a need to remove excess thionyl chloride by boiling with toluene.

For amidation, 1,4-dioxane (carcinogen) is used, which is not preferable for human body.

For amidation, a large excess of ammonia is used to avoid hydrolysis of 2, which causes a large amount of ammonia gas generated during dehydration and ring closure. The amount generated is about 400-fold volume relative to camphorsulfonic acid, which makes industrial production unattainable.

For the reduction step, an aqueous methanol solution is used, which causes hydrolysis of sodium borohydride, which uneconomically necessitates addition of excess sodium borohydride. What is more, an excess hydrogen gas is generated.

The obtained 5 is extracted with methylene chloride (environmental contaminant), and the resulting organic layer is washed and condensed, after which 5 is recrystallized from ethanol for isolation. During these steps, crystals adhere to the wall of the container (scaling), which is industrially undesirable.

When the above-mentioned conventional production method is industrially applied, therefore, various problems occur. Thus, the development of an industrially applicable production method of camphorsultam and an intermediate thereof is demanded, which is less associated with the above-mentioned problems (production cost, production efficiency, influence on human body and the environment, simplicity and easiness, safety of reaction etc.).

It is therefore an object of the present invention to provide an industrially applicable production method of camphorsultam and an intermediate thereof, which is comparatively safe to the environment and human body, economical, simple and easy.

SUMMARY OF THE INVENTION

According to the present invention, it has been found that the use of an aqueous isopropanol solution in the reduction step makes hydrolysis of sodium borohydride difficult, as a result of which the use of sodium borohydride in excess is obliterated and the amount of generated hydrogen gas is decreased. It has been also found that, when camphorsulfonyl halide is reacted with aqueous ammonia in a solvent immiscible with water during amidation, hydrolysis of camphorsulfonyl halide can be inhibited, which in turn more preferably reduces considerably the amount of ammonia to be used. Furthermore, by using an acid instead of extracting with an environment polluting substance, such as methylene chloride, after reduction, camphorsultam can be obtained as crystals.

Thus, the present invention relates to a production method of camphorsultam (10,10-dimethyl-3-thia-4-azatricyclo [5.2.1.0$^{1,5}$]decane 3,3-dioxide), which includes reduction of camphorsulfonimine (10,10-dimethyl-3-thia-4-azatricyclo [5.2.1.0$^{1,5}$]dec-4-ene 3,3-dioxide) with sodium borohydride in an aqueous isopropanol solution, wherein sodium borohydride is preferably used in a 0.3-fold to 0.7-fold molar amount relative to camphorsulfonimine.

More particularly, the present invention relates to a method for producing camphorsultam, which includes the following steps:

Step 1: reacting camphorsulfonic acid ((7,7-dimethyl-2-oxobicyclo[2.2.1]hept-1-yl)methanesulfonic acid) with a halogenation agent to give camphorsulfonyl halide ((7,7-dimethyl-2-oxobicyclo[2.2.1]hept-1-yl) methanesulfonyl halide), Step 2: reacting the camphorsulfonyl halide with ammonia to give camphorsulfonamide ((7,7-dimethyl-2-oxobicyclo[2.2.1]hept-1-yl)methanesulfonamide), Step 3: subjecting the camphorsulfonamide to dehydration and ring closure to give camphorsulfonimine, and Step 4: reducing the camphorsulfonimine with sodium borohydride in an aqueous isopropanol solution to give camphorsultam.

In Step 2, camphorsulfonyl halide is preferably reacted with aqueous ammonia in a solvent immiscible with water, and the aqueous ammonia preferably contains ammonia in a 4-fold to 10-fold molar amount relative to camphorsulfonyl halide.

In Step 4, sodium borohydride is preferably used in a 0.3-fold to 0.7-fold molar amount relative to camphorsulfonimine.

After Step 4, an acid may be added to the reaction mixture to allow precipitation of camphorsultam. The acid used at this time is preferably hydrochloric acid.

DETAILED DESCRIPTION OF THE INVENTION

The present invention is explained in detail in the following.

Camphorsultam can be obtained by successively conducting halogenation, amidation, ring closure and reduction, using camphorsulfonic acid as a starting material. In the present invention, camphorsultam encompasses a racemate and optically active compounds (1S and 1R).

Step 1 (Halogenation)

Camphorsulfonic acid is reacted with a halogenation agent to give camphorsulfonyl halide. To be specific, camphorsulfonic acid is added to a solvent, and a halogenation agent is added thereto (preferably by dropwise addition) to give camphorsulfonyl halide.

The solvent used in Step 1 is preferably toluene, xylene, cyclohexane, monochlorobenzene, nitrobenzene and the like, with particular preference given to toluene.

The solvent is generally used in an amount of 70 parts by weight—300 parts by weight, preferably 80 parts by weight—150 parts by weight, per 100 parts by weight of camphorsulfonic acid. When the amount thereof is less than 70 parts by weight per 100 parts by weight of camphorsulfonic acid, the stirring becomes difficult, and when it exceeds 300 parts by weight, the reaction time becomes longer. When the above-mentioned preferable solvents are used as reaction solvents, the amount of the halogenation agent can be reduced as compared to that in a non-solvent system, even without using methylene chloride, which has been conventionally employed for halogenation and which is an environment polluting substance. This has an effect that a step for removing an excess halogenation agent is not necessary.

The halogenation agent is not subject to any particular limitation as long as it can be used for halogenation in this step, and exemplified by thionyl chloride, thionyl bromide, oxalyl chloride, phosphorus oxychloride and the like, which is preferably thionyl chloride from an economical standpoint.

The amount of the halogenation agent varies depending on the kind of the halogenation agent to be used but may be any amount as long as halogenation proceeds sufficiently. For example, the amount of thionyl chloride as a halogenation agent is generally 1.0 mol–1.5 mol, preferably 1.0 mol–1.2 mol, per 1 mol of camphorsulfonic acid. When its amount is less than 1.0 mol per 1 mol of camphorsulfonic acid, halogenation becomes insufficient, and when it exceeds 1.5 mol, the reaction becomes costly.

The halogenation is preferably accelerated by adding N,N-dimethylformamide. N,N-dimethylformamide can be added to a solvent along with camphorsulfonic acid, wherein its amount is preferably 0.001 part by weight–0.5 part by weight per 100 parts by weight of camphorsulfonic acid.

The halogenation is generally conducted at a temperature of from room temperature to the refluxing temperature of the solvent used, which is preferably 70° C.–90° C. for the smooth progress of the reaction. The completion of the halogenation can be confirmed by gas chromatography (GC), and the halogenation generally ends in 1 h–4 h. It is also preferable to add a halogenation agent (preferably by dropwise addition) at a temperature within the above-mentioned range for the acceleration of the reaction. The reaction between a halogenation agent and camphorsulfonic acid produces a toxic gas (SO$_2$, hydrogen halide). However, the dropwise addition of the halogenation agent makes it possible to control the rate of generation of the toxic gas. It is also possible to add dropwise a halogenation agent after adding an absorbent (e.g., triethylamine, dimethylaniline, pyridine etc.) to the system. The dropwise addition of the halogenation agent is generally completed in about 30 min to 8 h, which is subject to change depending on the amount of the halogenation agent used.

Camphorsulfonyl halide can be isolated and purified by conventional methods, but may be used for the next Step 2 (amidation) without isolation.

Step 2 (Amidation)

Camphorsulfonamide can be obtained by reacting camphorsulfonyl halide with ammonia. Preferably, camphorsulfonyl halide is reacted with aqueous ammonia in a solvent immiscible with water to give camphorsulfonamide. To be specific, aqueous ammonia is added to a solvent immiscible with water, and camphorsulfonyl halide is added thereto (preferably by dropwise addition after dissolution in a solvent immiscible with water). This method is beneficial because the reaction proceeds in two phases by the use of a solvent immiscible with water and aqueous ammonia, thereby avoiding hydrolysis of camphorsulfonyl halide (camphorsulfonyl halide dissolves in a solvent immiscible with water), which in turn reduces the amount of ammonia used, and consequently, the amount of ammonia gas generated in the next step (ring closure).

The solvent immiscible with water usable for amidation is exemplified by toluene, xylene, monochlorobenzene, dichlorobenzene and heptane. The solvent used in the previous step (halogenation) is preferably used, because the reaction mixture after halogenation can be used as it is, which makes the operation simple and easy.

The solvent immiscible with water is generally used in an amount of 100 parts by weight–400 parts by weight, preferably 180 parts by weight–250 parts by weight, per 100 parts by weight of camphorsulfonyl halide (camphorsulfonic acid when amidation is carried out directly after halogenation).

As the ammonia, ammonia gas, aqueous ammonia and the like can be used. Aqueous ammonia can be preferably used in view of the easiness of use and economical aspect. It is generally used at a concentration of 20 wt %–30 wt %, preferably 28 wt %.

The amount of ammonia used is not subject to any particular limitation as long as amidation can be conducted, and is preferably 4 mol–10 mol, more preferably 5 mol–7 mol, per 1 mol of camphorsulfonyl halide (camphorsulfonic acid when amidation is carried out directly after halogenation). When the amount is less than 4 mol per 1 mol of camphorsulfonyl halide, the amount of obtained camphorsulfonamide decreases, whereas when it exceeds 10 mol, ammonia gas is generated in a large amount in the next step (ring closure), which makes the industrial application difficult.

The amidation is preferably conducted efficiently by dissolving camphorsulfonyl halide in a solvent immiscible with water and adding dropwise the resulting solution to aqueous ammonia. The dropwise addition is generally completed in about 15 min to 8 h, preferably 30 min to 5 h, generally at −15° C. to 50° C., preferably −10° C. to 25° C., which is subject to change depending on the amount used of camphorsulfonyl halide.

The amidation is conducted generally at −15° C. to 50° C., preferably −10° C. to 25° C. The completion of the amidation can be confirmed by GC, and the amidation generally ends in 2 h to 4 h, which is subject to change depending on the reaction scale.

Camphorsulfonamide can be isolated and purified by conventional methods, or can be used as it is for the next Step 3 (ring closure).

Step 3 (Ring Closure)

Camphorsulfonimine can be obtained by heating camphorsulfonamide for dehydration and ring closure. Preferably, the reaction mixture obtained according to the preferable method in the above-mentioned Step2 is heated further to give camphorsulfonimine. Camphorsulfonamide obtained by the above-mentioned amidation can be used conveniently and easily. In addition, since the amount of ammonia used for amidation is small, only a small amount of ammonia gas is generated during ring closure, which is preferable.

In the ring closure step, the temperature is preferably raised stepwise because the amount of the ammonia gas generated can be controlled thereby. Preferably, for example, after the completion of the amidation, (1) the reaction mixture is maintained at 55° C.–70° C. for 1 h, heated to 80° C.–85° C. and reacted at the same temperature for 1 h –3 h, or (2) the reaction mixture is heated to 80° C.–85° C. over 30 min–6 h, and reacted at a temperature in this range for 1 h–4 h.

The completion of the ring closure can be confirmed by GC.

Camphorsulfonimine is preferably isolated by cooling the reaction mixture stepwise, thereby to prevent scaling and improve crystallinity. For example, the reaction mixture is cooled to about 60° C. over 10 min or more and maintained (aged) at 50° C.–60° C. for 10 min–30 min. The mixture is then cooled to about 20° C. over 30 min or more, stirred at 10° C.–25° C. for 30 min–3 h, filtered and washed. It is preferably washed with toluene and then with water. Since impurities and inorganic substances are removed by washing, highly pure wet crystals having a GC purity of not less than 99% can be obtained. The obtained wet crystals may be dried under reduced pressure at not more than 100° C., or may be subjected to the next Step 4 (reduction) without drying.

Step 4 (Reduction)

Camphorsultam can be obtained by reducing camphorsulfonimine with sodium borohydride in a solvent. When the solvent is an aqueous isopropanol solution, sodium borohydride is not used in excess because it is hardly decomposed, which in turn further reduces the amount of hydrogen gas generated.

The aqueous isopropanol solution to be used for reduction is defined based on the amounts of isopropanol and water as follows. The amount of isopropanol to be used is generally 200 parts by weight–400 parts by weight, preferably 250 parts by weight–350 parts by weight, per 100 parts by weight of camphorsulfonimine (dry product). The amount of water to be used is generally 50 parts by weight–200 parts by weight, preferably 80 parts by weight–150 parts by weight, per 100 parts by weight of camphorsulfonimine (dry product). When wet crystals of camphorsulfonimine are used, the amount of water contained in the crystals should be included in the amount of the above-mentioned water used.

The amount of sodium borohydride to be used is preferably 0.3 mol–0.7 mol, more preferably 0.4 mol–0.6 mol, per 1 mol of camphorsulfonimine (dry product). When the amount of use is less than 0.3 mol per 1 mol of camphorsulfonimine (dry product), reduction becomes insufficient, and when it exceeds 0.7 mol, the reaction becomes costly. Sodium borohydride is preferably added dropwise in the form of an aqueous solution, because the addition in this manner affords constant generation of hydrogen gas and easy industrial operation. The dropwise addition is generally performed at 0° C. to the refluxing temperature of the solvent used, preferably 20° C.–45° C. The amount of water necessary for dissolving sodium borohydride is generally 300 parts by weight–800 parts by weight, preferably 400 parts by weight–600 parts by weight, per 100 parts by weight of sodium borohydride.

Furthermore, when sodium borohydride is used in the form of an aqueous solution, alkali metal hydroxide is preferably added to render the aqueous sodium borohydride solution more stable. Examples of alkali metal hydroxide include sodium hydroxide, potassium hydroxide and the like, with preference given to sodium hydroxide from the economical aspect. The alkali metal hydroxide is generally used in an amount of 1 part by weight–4 parts by weight, preferably 2 parts by weight–3 parts by weight, per 100 parts by weight of sodium borohydride.

Reduction accompanies generation of hydrogen gas. It is therefore preferable to conduct reduction in an inert gas (e.g., nitrogen gas) atmosphere.

The reduction is generally conducted at 0° C. to the refluxing temperature of the solvent used, preferably 20° C. to 45° C. The completion of the reduction can be confirmed by GC, and the reduction generally ends in about 2 h to 8 h, preferably 4 h to 6 h, though subject to change depending on the amount of camphorsulfonimine used.

Camphorsultam can be preferably isolated by dropwise addition of acid and water to the reaction mixture, rather than extraction with an organic solvent, such as methylene chloride, because the former method does not give rise to scaling and is industrially applicable. The acid to be used for isolation is preferably hydrochloric acid. The acid may be used in any amount as long as the reaction mixture can be generally adjusted to not more than pH 3, preferably not more than pH 1.

To be specific, the reaction mixture is cooled to 10° C.–20° C., and the acid is added (preferably by dropwise addition) to adjust the pH of the reaction mixture to not more than 3, preferably not more than 1, whereby crystals are precipitated. The acid is added dropwise generally at 10° C.–30° C. for about 5 min–2 h, though subject to change depending on the amount of camphorsulfonimine.

After the addition of the acid, generally 200 parts by weight–300 parts by weight of water is added dropwise per 100 parts by weight of camphorsulfonimine (dry product) at 10° C.–30° C. over 15 min–2 h. The reaction mixture is then cooled to 0° C., preferably 0° C.–5° C., and stirred at the same temperature for 30 min–15 h. The reaction mixture is filtered, and the resulting crystals are washed to remove inorganic substances and dried.

For washing, a mixture of isopropanol and water is cooled to about 0° C.–5° C. and used. Isopropanol and water are preferably used in an amount of 20 parts by weight–40 parts by weight and 30 parts by weight–50 parts by weight, respectively, per 100 parts by weight of camphorsulfonimine (dry product).

Camphorsultam can be dried under reduced pressure at generally not more than 100° C., preferably 50° C.–80° C., to a water content of not more than 1% by the Karl Fischer method (KF method). By the aforementioned series of steps for isolation and purification, camphorsultam having a purity of 99%–100% can be obtained.

The present invention is explained in more detail in the following by referring to Examples, which do not limit the present invention in any way. In $^1$H-NMR, the unit of J is Hz without exception.

EXAMPLE 1

Production of (−)-10,10-dimethyl-3-thia-4-azatricyclo[5.2.1.0$^{1,5}$]dec-4-ene 3,3-dioxide (camphorsulfonimine)

N,N-Dimethylformamide (230 g) and (1S)-(+)-10-camphorsulfonic acid (190 kg, 818 mol) were added to toluene (190 L), and thionyl chloride (116.8 kg, 982 mol) was added in a thin stream at 70° C.–80° C. over 2 h, and the mixture was stirred at the same temperature for 2 h. The obtained solution of camphorsulfonyl chloride in toluene was added dropwise at −10° C. to 25° C. over 3 h to a mixture of 28 wt % aqueous ammonia (248.7 kg, 4.1 kmol) and toluene (277 L), which mixture had been separately prepared and cooled to −10° C. to −5° C. The container of acid chloride was washed with toluene (29 L) and the washing was added to the reaction mixture, which was followed by stirring at 10° C.–25° C. for 2 h. The reaction mixture was heated to 80° C. over 85 min and stirred at 80° C.–83.3° C. for 3 h. The amount of the ammonia gas generated was 39 m$^3$. The reaction mixture was cooled to 60° C. over 20 min and aged at 54° C.–60° C. for 15 min. The reaction mixture was cooled to 20° C. over 1 h and stirred at 15° C.–20° C. for 40 min. The reaction mixture was filtered at 15° C. and washed successively with toluene (57 L) and water (380 kg) to give wet crystals (177.1 kg). The crystals were partially dried and analyzed. As a result, the crystals contained the title compound in an amount of 144.7 kg (yield 83%).

$^1$H-NMR (CDCl$_3$) δ:0.87 (s, 3H), 1.09 (s, 3H), 1.48 (m, 1H), 1.78 (m, 1H), 2.07 (m, 2H), 2.26 (m, 1H), 2.39 (d, 1H, J=20), 2.80 (dm, 1H, J=19), 2.98 (d, 1H, J=13), 3.18 (d, 1H, J=14).

EXAMPLE 2

Production of (−)-10,10-dimethyl-3-thia-4-azatricyclo[5.2.1.0$^{1,5}$]decane 3,3-dioxide (camphorsultam)

The wet crystals (177 kg) obtained in Example 1 were added to a mixture of isopropanol (457.4 kg) and water (112 kg) in a nitrogen gas atmosphere, and a solution of sodium hydroxide (280 g) and sodium borohydride (12.9 kg) in water (72.3 kg) was added dropwise at 30° C.–40° C. for 2 h. The mixture was stirred in a nitrogen gas atmosphere at the same temperature for 2 h, after which the completion of the reaction was confirmed by GC.

The reaction mixture was cooled to 10° C.–20° C., and 35% hydrochloric acid was added at 10° C.–30° C. over 1 h, and the reaction mixture was adjusted to pH 1 to allow precipitation of crystals. The amount of 35% hydrochloric acid used then was 42.4 kg. Water (326 kg) was added dropwise at 14° C.–19° C. over 1 h, and the mixture was stirred at 0° C.–5° C. for 1 h and filtered. The resulting crystals were washed with a mixture of isopropanol (45.7 kg) and water (58 kg). The crystals were dried at 55° C.–80° C. under reduced pressure to give the title compound (114.1 kg) (yield 78%, purity 99.99%).

$^1$H-NMR (CDCl$_3$) δ:0.94 (s, 3H), 1.13 (s, 3H), 1.31 (m, 1H), 1.46 (m, 1H), 1.84–2.00 (m, 5H), 3.08 (d, 1H, J=14), 3.16 (d, 1H, J=14), 3.42 (m, 1H), 4.13 (brs, 1H).

EXAMPLE 3

Production of (+)-10,10-dimethyl-3-thia-4-azatricyclo[5.2.1.0$^{1,5}$]dec-4-ene 3,3-dioxide (camphorsulfonimine)

N,N-Dimethylformamide (0.5 ml) and (1R)-(−)-10-camphorsulfonic acid (400 g, 1.722 mol) were added to toluene (400 ml), and thionyl chloride (245.83 g, 2.066 mol) was added dropwise at 74° C.–77° C. over 2 h 10 min. The mixture was stirred at 77° C.–78° C. for 2 h. The obtained solution of camphorsulfonyl chloride in toluene was added dropwise at 2° C.–16° C. over 90 min to a mixture of 28 wt % aqueous ammonia (523.6 g, 8.61 mol) and toluene (540 ml), which mixture had been separately prepared and cooled to −5° C. to 0° C. The container of acid chloride was washed with toluene (60 ml) and the washing was added to the reaction mixture, which was followed by stirring at 16° C.–22° C. for 2 h. The reaction mixture was heated to 80° C. over 55 min, and the mixture was stirred at 80° C.–85° C. for 2 h. The reaction mixture was cooled to 60° C. over 25 min and aged at 51° C.–60° C. for 15 min. The reaction mixture was cooled to 20° C. over 40 min, and the mixture was stirred at 17° C.–20° C. for 2 h. The reaction mixture was filtered and washed successively with toluene (120 ml) and water (800 ml) to give wet crystals (329.71 g). The crystals were dried at 50° C.–60° C. under reduced pressure to give the title compound (283.96 g, yield 77.3%, purity 99.9% (GC)).

$^1$H-NMR (CDCl$_3$) δ:0.87 (s, 3H), 1.09 (s, 3H), 1.47 (m, 1H), 1.79 (m, 1H), 2.06 (m, 2H), 2.26 (m, 1H), 2.39 (d, 1H, J=19), 2.77 (dm, 1H, J=19), 2.97 (d, 1H, J=13), 3.18 (d, 1H, J=13).

EXAMPLE 4

Production of (+)-10,10-dimethyl-3-thia-4-azatricyclo[5.2.1.0$^{1,5}$]decane 3,3-dioxide (camphorsultam)

The crystals (214.8 g, 1.007 mol) obtained in Example 3 were added to a mixture of isopropanol (674 g) and water (214.8 g) in a nitrogen gas atmosphere, and a solution of sodium hydroxide (410 mg) and sodium borohydride (19.1 g) in water (107.4 g) was added dropwise at 31° C.–43° C. over 2 h 34 min. The mixture was stirred in a nitrogen gas atmosphere at 30° C.–40° C. for 6 h, after which the completion of the reaction was confirmed by GC. Since the starting material remained in a proportion of 3.4%, a solution of sodium borohydride (2.86 g) and sodium hydroxide (60 mg) in water (16.1 ml) was again prepared and added dropwise to the reaction mixture in a nitrogen gas atmosphere at 38° C. over 2 min. The mixture was stirred at 78° C.–83° C. for 3 h 30 min.

The reaction mixture was cooled to 15° C. and 35% hydrochloric acid was added at the same temperature over 8 h to adjust the reaction mixture to pH 1, thereby to allow precipitation of crystals. The amount of the 35% hydrochloric acid used then was 72.4 g. Water (537 g) was added at 15° C. over 19 min and the mixture was cooled to 5° C. The reaction mixture was stirred at 0° C.–3° C. for 15 h and filtered. The resulting crystals were washed with a cooled mixture of isopropanol (46.5 g) and water (86 g). The crystals were dried at 55° C.–60° C. under reduced pressure to give the title compound (153.42 g, yield 70.8%, purity 99.97%).

$^1$H-NMR (CDCl$_3$) δ:0.94 (s, 3H), 1.13 (s, 3H), 1.31 (m, 1H), 1.46 (m, 1H), 1.86–2.01 (m, 5H), 3.09 (d, 1H, J=14), 3.14 (d, 1H, J=14), 3.44 (m, 1H), 4.07 (brs, 1H).

It is expected that, when, under the conditions of Capet et al., the same amount of (1S)-(+)-10-camphorsulfonic acid as used in Example 1 is chlorinated and the resulting chlorinate is amidated with aqueous ammonia containing a 60-fold molar amount of ammonia relative to (1S)-(+)-10-camphorsulfonic acid and heated for ring closure, 753 m$^3$ of ammonia gas will be generated. In contrast, only 39 m$^3$ of ammonia gas was generated in Example 1, which result establishes that the method of the present invention is industrially preferable.

According to the present invention, camphorsultam and intermediates thereof, which are useful as a reagent for asymmetric induction and as a starting material of fine chemicals and medicaments, can be obtained by an industrially applicable production method, which is comparatively safe to the environment and human body, economical, and which is simple and easy.

This application is based on patent application No. 253083/2000 filed in Japan, the contents of which are hereby incorporated by reference.

What is claimed is:

1. A method for producing camphorsultam, which comprises the steps of:
    Step 1: reacting camphorsulfonic acid with thionyl chloride in toluene to give camphorsulfonyl halide,
    Step 2: reacting the camphorsulfonyl halide with ammonia to give camphorsulfonamide,
    Step 3: subjecting the camphorsulfonamide to dehydration and ring closure to give camphorsulfonimine, and
    Step 4: reducing the camphorsulfonimine with sodium borohydride in an aqueous isopropanol solution.

2. The method of claim 1, wherein, in Step 2, the ammonia is aqueous ammonia and the reaction is carried out in a solvent immiscible with water.

3. The method of claim 2, wherein the aqueous ammonia comprises ammonia in a 4-fold to 10-fold molar amount relative to the camphorsulfonyl halide.

4. The method of claim 1, wherein, in Step 4, sodium borohydride is used in a 0.3-fold to 0.7-fold molar amount relative to the camphorsulfonimine.

5. The method of claim 1, which further comprises adding an acid to the reaction mixture after Step 4 to precipitate camphorsultam.

6. The method of claim 5, wherein the acid is hydrochloric acid.

7. The method of claim 2, which further comprises adding an acid to the reaction mixture after Step 4 to precipitate camphorsultam.

8. The method of claim 7, wherein the acid is hydrochloric acid.

9. The method of claim 3, which further comprises adding an acid to the reaction mixture after Step 4 to precipitate camphorsultam.

10. The method of claim 9, wherein the acid is hydrochloric acid.

11. The method of claim 4, which further comprises adding an acid to the reaction mixture after Step 4 to precipitate camphorsultam.

12. The method of claim 11, wherein the acid is hydrochloric acid.

* * * * *

UNITED STATES PATENT AND TRADEMARK OFFICE
CERTIFICATE OF CORRECTION

PATENT NO.    : 6,441,187 B1                                          Page 1 of 1
DATED         : August 27, 2002
INVENTOR(S)   : Shiratani et al.

It is certified that error appears in the above-identified patent and that said Letters Patent is hereby corrected as shown below:

Title page,
Item [75], Inventors, "Yamasaki" should read as -- Yamazaki --.
Item [73], Assignees, "Pharmaceuticals" should read as -- Pharmaceutical --.
Item [56], References Cited, OTHER PUBLICATIONS  second reference,
"[3+2] Cycloadditionen" should read as -- "[3+2]-Cycloadditionen --.

Column 1,
Line 18, "pounds" should read as -- compounds --.

Signed and Sealed this

Fourth Day of March, 2003

JAMES E. ROGAN
*Director of the United States Patent and Trademark Office*